(12) United States Patent
Johanning

(10) Patent No.: US 10,094,342 B2
(45) Date of Patent: Oct. 9, 2018

(54) FUEL VAPORIZER SYSTEM WITH FUEL INJECTION

(71) Applicant: BIXBY ENERGY SYSTEMS, INC., Wilmington, DE (US)

(72) Inventor: Dean Johanning, Campbellsport, WI (US)

(73) Assignee: BIXBY ENERGY SYSTEMS, INC., Wilmington, DE (US)

( * ) Notice: Subject to any disclaimer, the term of this patent is extended or adjusted under 35 U.S.C. 154(b) by 14 days.

(21) Appl. No.: 15/456,189

(22) Filed: Mar. 10, 2017

(65) Prior Publication Data

US 2017/0260935 A1 Sep. 14, 2017

Related U.S. Application Data

(60) Provisional application No. 62/307,042, filed on Mar. 11, 2016.

(51) Int. Cl.
*F02M 31/18* (2006.01)
*F02M 31/135* (2006.01)
*F02M 31/08* (2006.01)
*F02M 31/087* (2006.01)

(52) U.S. Cl.
CPC ........ *F02M 31/183* (2013.01); *F02M 31/087* (2013.01); *F02M 31/0825* (2013.01); *F02M 31/135* (2013.01); *Y02T 10/126* (2013.01)

(58) Field of Classification Search
CPC .... Y02T 10/123; F02M 31/18; F02M 31/087; F02M 19/03; F02M 17/28; F02M 29/04; F02M 69/047; F02M 35/10216; F02M 53/02
See application file for complete search history.

(56) References Cited

U.S. PATENT DOCUMENTS

| | | | | |
|---|---|---|---|---|
| 3,911,881 A | * | 10/1975 | Lee, Jr. | ..................... F01N 3/10 123/545 |
| 4,510,913 A | * | 4/1985 | deCelle | .................. F02M 31/18 123/482 |
| 5,035,227 A | | 7/1991 | Hansen | |

(Continued)

OTHER PUBLICATIONS

WIPO; International Search Report and Written Opinion mailed in counterpart International Patent Application No. PCT/US 17/22186 dated Jun. 20, 2017.

*Primary Examiner* — Long T Tran
(74) *Attorney, Agent, or Firm* — Fish & Richardson P.C.

(57) ABSTRACT

A fuel vaporizer including fuel injectors is described herein. The vaporizer includes a housing having a plurality of baffles defining a plurality of chambers, with each of the plurality of baffles defining an aperture between adjacent chamber, and the apertures define a flow path from the air inlet, through the plurality of chambers, and to the vapor outlet. A conduit extends through the baffles and chambers, and the conduit is adapted to accept a flow exhaust gas and transfer thermal energy from the exhaust gas to an airflow along the flow path A fuel injector is positioned in the housing to inject fuel into the flow path in the first chamber, the thermal energy from the conduit vaporizing the fuel injected into the airflow and producing the flow of vaporized fuel. The fuel vaporizer may include a heat exchanger pre-heating the airflow and electric heating elements supplementing the conduit heating.

26 Claims, 7 Drawing Sheets

(56) References Cited

U.S. PATENT DOCUMENTS

| | | | |
|---|---|---|---|
| 5,040,518 A | 8/1991 | Hamm | |
| 5,291,870 A | 3/1994 | Covey, Jr. | |
| 5,746,188 A * | 5/1998 | Cooke | F02M 31/18 |
| | | | 123/549 |
| 5,782,225 A * | 7/1998 | Caggiano | F02G 5/00 |
| | | | 123/545 |
| 6,189,518 B1 * | 2/2001 | Cooke | F02M 31/12 |
| | | | 123/549 |
| 2008/0078363 A1 | 4/2008 | Apperson | |
| 2010/0295193 A1 | 11/2010 | Johanning | |

* cited by examiner

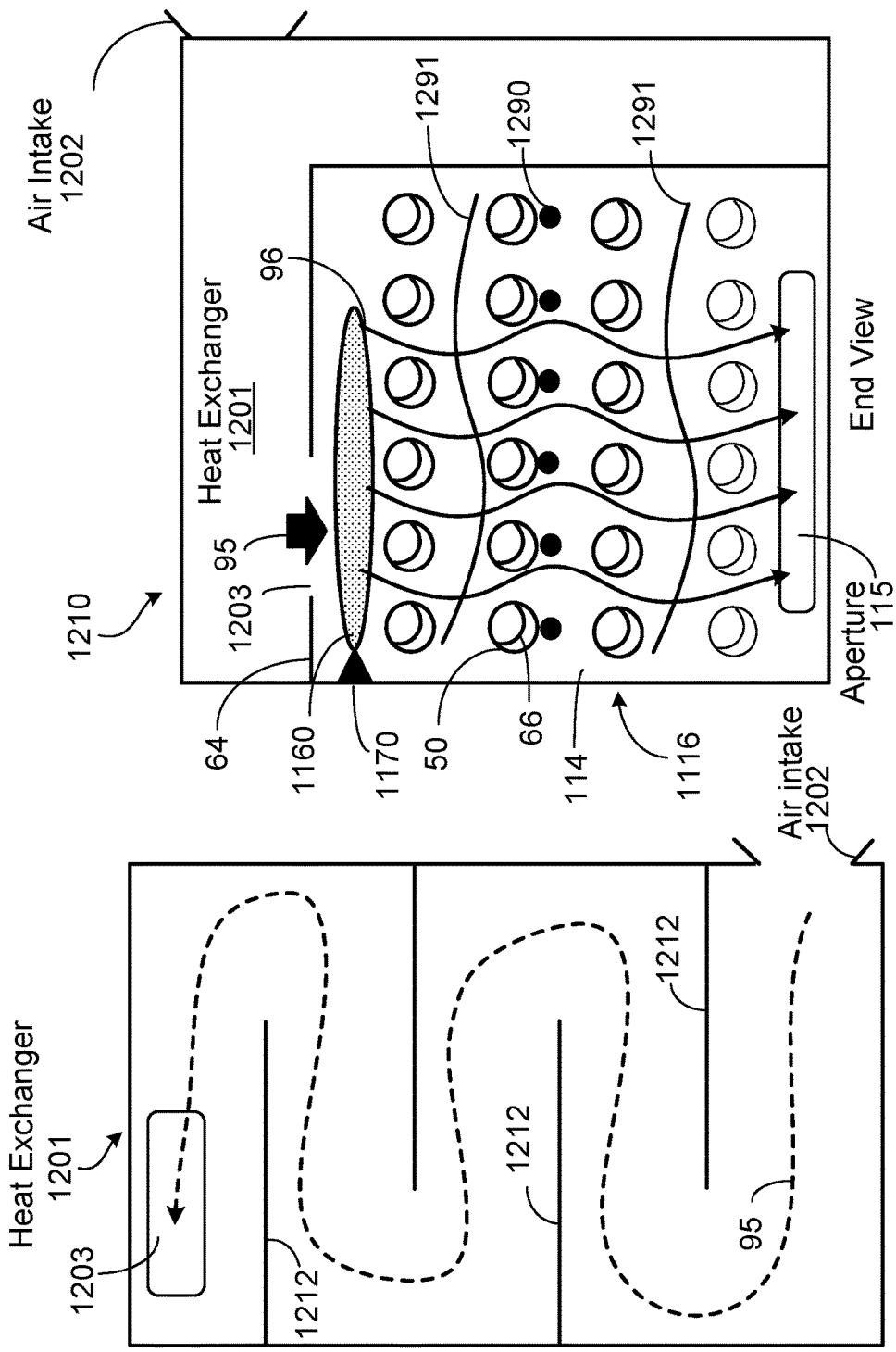

FUEL VAPORIZER SYSTEM WITH FUEL INJECTION

FIELD

The present invention relates to fuel conditioning systems and more particularly to conditioning systems that vaporize the fuel to achieve enhanced energy recovery.

BACKGROUND

Consumers have long demanded higher fuel efficiency. One line of technological development to meet this demand has involved changing the structure of the vehicle. Size, shape and offered features impact the miles per gallon. Perhaps the most efficient of vehicles using this line of technology is the motorcycle, which most commonly get about fifty miles to the gallon.

Another line of technology focuses on the fuel itself. People have known that liquid fuel does not burn. Vapors around the liquid will burn. In fact, chemists will state that if one could put a lit match into liquid fuel in the absence of vapors, the match will extinguish. In typical vehicles, some believe that only about 18% of the fuel is in vapor form prior to and during ignition in the internal combustion engines. The balance of the fuel is sent out of the vehicle through the exhaust system. The catalytic converter conditions the unconsumed fuel prior to release into the atmosphere. Technology, focusing on conditioning of the fuel, vaporizes a greater percentage of the fuel, thereby gaining an improve energy recovery.

Generally, the vaporizing devices use excess energy from the engine. Heat energy can be drawn off the exhaust or cooling system. Some use the excess electrical energy as an energy supply. This energy is transmitted to the fuel usually in one of a few manners. The most popular appear to be mist vaporizers and boilers.

Mist vaporizing systems in general terms atomize the fuel into a mist form and apply heat to convert the mist into a vapor. These systems take advantage of the fact that mist, has far greater surface area, making it more readily converted to vapor, than a pool of fuel. Unfortunately these mist vaporizing systems are generally not operational until after the vehicle has warmed, since the atomized fuel tends to pool before heat is abundant and pooling fouls the system. Wasteful adaptation to address the pooling are found in most of these systems.

As an example, Covey Jr. (U.S. Pat. No. 5,291,900) discloses a Fuel Vaporizing System. The system has an inner and outer housing with a temperature probe therebetween. Exhaust passes between the inner and outer housings. Atomized fuel is injected into the inner housing. The fuel, mist form, is converted to vapor as it rises through a series of baffles. This system, by its own admission, is not operational until the probe detects a temperature of at least 550 degree F. The waste here is in not being able to use the system until the vehicle has warmed well and the waste is experienced in cold climates and on short trips.

Covey Jr. (U.S. Pat. No. 4,368,163) discloses an Apparatus for Vaporizing Fuel for Engine in Conjunction with Carburetor. Atomized fuel is sprayed at a conduit containing exhaust. The conduit, a heat exchanger, causes the mist to vaporize. Any mist that fails to vaporize pools in a well and is drained back into the fuel line. This invention is wasteful in requiring additional apparatus to merge two streams of fuel and having lower vapor production in cold climates and on short trips.

A boiler system may be used to evaporate fuel from a pool of liquid fuel. This has the advantage of being useable before the exhaust or cooling systems are fully heated. However, boilers are inefficient and have lower vapor production in that they do not take advantage of the well accepted atomizer technology, which greatly increases the surface area of the fuel and eases the conversion liquid fuel to vapor.

For example, Lahti et al. (U.S. Pat. No. 6,415,775) discloses a Preheat Fuel Delivery System. This system directs air through a bubbler tank. Vapors are collected above the pool of fuel. Advantageously, this system will work when fuel pools. Unfortunately, the surface area from which the fuel may vaporize is greatly reduced from the surface area that would be present should the fuel be heated from a mist form. This system compensates for low vapor production, routing exhaust into the bubbler, which unfortunately mixes carbon dioxide (not oxygen) with the vaporized fuel.

Cook (U.S. Pat. No. 5,746,188) discloses another example of a boiler system entitled Apparatus for Supplying Fuel to an Internal Combustion Engine. Liquid fuel is injected into the interior of the housing. The liquid fuel passes through openings in the baffles gathering heat and eventually vaporizing prior to exiting the housing. Advantageously, this system will work when fuel pools. Unfortunately, the surface area from which the fuel may vaporize is greatly reduced from the surface area that would be present should the fuel be heated from a mist form, yielding lower vapor production.

What is needed is a fuel vaporization system that vaporizes fuel while in a mist form and yet will also vaporize, e.g., boil, fuel while in a pooled form. The system should avoid the waste attendant with evacuating or avoiding pooled fuel and likewise should capture the higher vapor production attainable when vaporizing fuel in a mist form. Desirably, the components are minimal and are used both for vaporizing the mist and boiling the fuel pools.

SUMMARY OF THE INVENTION

Certain aspects of the present disclosure relate to a fuel vaporization system that vaporizes fuel while in a mist form and simultaneously vaporizes, e.g., boils, fuel while in a pooled form. Certain aspects avoid the waste attendant with evacuating or avoiding pooled fuel and likewise has the higher vapor production attainable the vaporizing fuel in a mist form. The components are minimal and are used both for vaporizing the mist and boiling the fuel pools, e.g. the systems are integrated.

One example is a fuel vaporizer having a fuel injection system. The fuel vaporizer includes a housing having a plurality of baffles joined to the housing, the housing and baffles defining a plurality of chambers, each of the plurality of baffles defining an aperture between adjacent chamber, an air inlet in a first chamber of the plurality of chambers, an vapor outlet in a last chamber of the plurality of chambers, the apertures defining a flow path from the air inlet, through the plurality of chambers, and to the vapor outlet, and a conduit extending through the baffles and chambers, the conduit adapted to accept a flow of exhaust gas therethrough, the conduit positioned in the flow path, and the conduit adapted to transfer thermal energy from the exhaust gas to an airflow along the flow path. The fuel vaporizer also includes a fuel injector positioned in an opening in the housing, with the fuel injector adapted to inject fuel into the flow path in the first chamber. The housing is adapted to accept the airflow at the air inlet and produce a flow of vaporized fuel to the vapor outlet. In operation, the thermal energy from the conduit vaporizes the fuel injected into the airflow and produces the flow of vaporized fuel.

In one example, the fuel vaporizer may include a housing joined to baffles. Conduit is in thermal communication with exhaust and is in thermal communication with fuel in a mist form. The conduit may also be in thermal communication with the baffles. The baffles are in thermal communication with the housing. The baffles and housing contain and are, at least optionally, in thermal communication with a pool of fuel.

In another example, the fuel vaporizer may include a housing. Conduit extends through the housing. At least one turbulator may be joined to the conduit.

Advantageously, the present invention combines the technologies of mist vaporizers and boilers in a single simplified unit.

As yet another advantage, the present invention simultaneously vaporizes fuel in a mist form and in a pooled liquid form.

As still yet another advantage, the present invention includes a turbulator to cause turbulence in the exhaust passing through the conduit, increasing thermal transfer from the exhaust to the conduit.

Further, the present invention uses the same conduit to transfer heat energy to a boiler and to fuel in a mist form.

Also as an advantage, the present invention utilizes a housing and baffles to define a fuel passageway and to define a boiler to contain fuel and vaporize fuel in a liquid form.

In some examples, the fuel vaporizer defines an exhaust inlet chamber and an exhaust outlet chamber in flowable fluid communication through the conduit. In some examples, conduit is a matrix of a plurality conduits. In some examples, the conduit includes a turbulator joined inside the conduit.

In some examples, the fuel vaporizer includes an electric heating element adapted to heat the conduit, the heating element enabling electric heating of the airflow through the flow path. The heating element may be integrated with the plurality of baffles. The heating element may be integrated with the conduit.

In some examples, the fuel vaporizer includes a heat exchanger in thermal connection with the outer surface of the housing. The heat exchanger defines an internal flow path in flowable fluid communication with the air inlet of the housing, and the heat exchanger is adapted to heat the airflow along the internal flow path with thermal energy from the housing prior to the airflow entering the air let of the housing.

In some examples, the fuel injector is a first fuel injector in a first opening in the housing, and the fuel vaporizer further includes a second fuel injector positioned in a second opening in the housing, with the second fuel injector adapted to inject fuel into the flow path in the first chamber.

In some examples, a second fuel injector is positioned in a second opening in the housing, with the second fuel injector adapted to inject fuel into the flow path in a second chamber, the second chamber being adjacent to the first chamber. In some examples a third fuel injector positioned in a third opening in the housing, with the third fuel injector adapted to inject fuel into the flow path in a third chamber, the third chamber being adjacent to the second chamber.

Another example is a method of operating an internal combustion engine, given a fuel, an airflow, and exhaust gas from the internal combustion engine. The method includes flowing the exhaust gas through a conduit, the conduit passing through a plurality of chambers formed by a plurality of baffles, the exhaust gas transferring thermal energy to the conduit, flowing the airflow through the plurality of chambers, the airflow flowing around the conduit, injecting the fuel in the airflow of a first chamber of the plurality of chambers, the injecting atomizing the fuel in the airflow, transferring thermal energy from the conduit to the airflow in the plurality of chambers, the thermal energy vaporizing at least a portion of the fuel in the airflow and generating a flow of vaporized fuel, and providing the flow of vaporized fuel to an intake of the internal combustion engine.

In some examples, flowing the exhaust gas through a conduit includes flowing the exhaust gas through a matrix of a plurality of conduits.

In some examples, flowing the airflow through the plurality of chambers including the airflow flowing through the matrix of the plurality of conduits in each of the plurality of chambers.

In some examples, flowing the exhaust gas through a conduit further includes adding turbulence to the flow of exhaust gas inside the conduit.

In some examples, the method includes injecting the fuel in the airflow in a second chamber of the plurality of chambers.

In some examples, transferring thermal energy from the conduit to the airflow in the plurality of chambers includes heating the airflow in the first chamber to at least 725 degrees Fahrenheit. In some examples, transferring thermal energy from the conduit to the airflow in the plurality of chambers includes heating the airflow in a last chamber to at least 450 degrees Fahrenheit.

In some examples, the thermal energy vaporizes at least 50% of the fuel. In some examples, the thermal energy vaporizes at least 80% of the fuel.

In some examples, the method further includes transferring thermal energy to the conduit with an electric heating element. In some examples, transferring thermal energy to the conduit with an electric heating element includes regulating a temperature of the airflow using the transferring of thermal energy to the conduit from the electric heating element. The regulating may be based on a temperature of one or more of the following: the exhaust gas, the conduit, and the airflow.

In some examples, flowing the exhaust gas through a conduit includes regulating the flow of exhaust gas through the conduit to maintain a temperature of the airflow in at least one of the first chamber and the intake.

In some examples, the method further includes, prior to the injecting the fuel in the airflow of a first chamber, starting the internal combustion engine using a fuel injection system of the internal combustion engine, and transitioning from the fuel injection system of the internal combustion engine to injecting the fuel in the airflow of a first chamber, the transitioning being based on a temperature of the airflow or a temperature of the conduit.

Yet another example is a method of operating an internal combustion engine, given a fuel, an airflow, and exhaust gas from the internal combustion engine. The method includes flowing the exhaust gas through a conduit, the conduit passing through a plurality of chambers formed by a plurality of baffles, flowing the airflow through the plurality of chambers, the airflow flowing around the conduit, injecting the fuel in the airflow of a first chamber of the plurality of chambers, the injecting atomizing the fuel in the airflow, transferring thermal energy from an electric heating element to the airflow in the plurality of chambers, the thermal energy vaporizing at least a portion of the fuel in the airflow and generating a flow of vaporized fuel, and providing the flow of vaporized fuel to an intake of the internal combustion engine.

These and other advantages will become apparent from reading the below description of the preferred embodiment with reference to the appended drawings.

BRIEF DESCRIPTION OF DRAWINGS

FIGS. 12A and 12B are schematics of a fuel vaporizer with fuel injectors and a heat exchanger.

Figure 1:
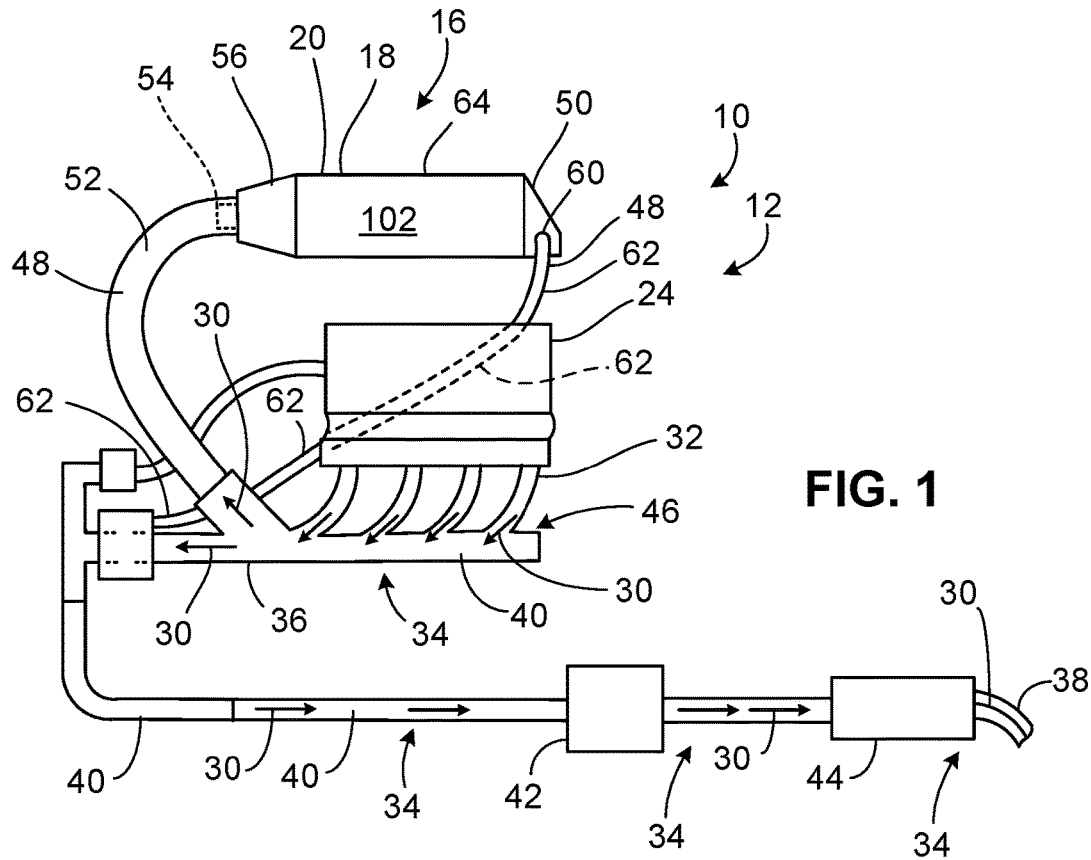
FIG. 1 is a schematic drawing of the exhaust system.
Figure 2:
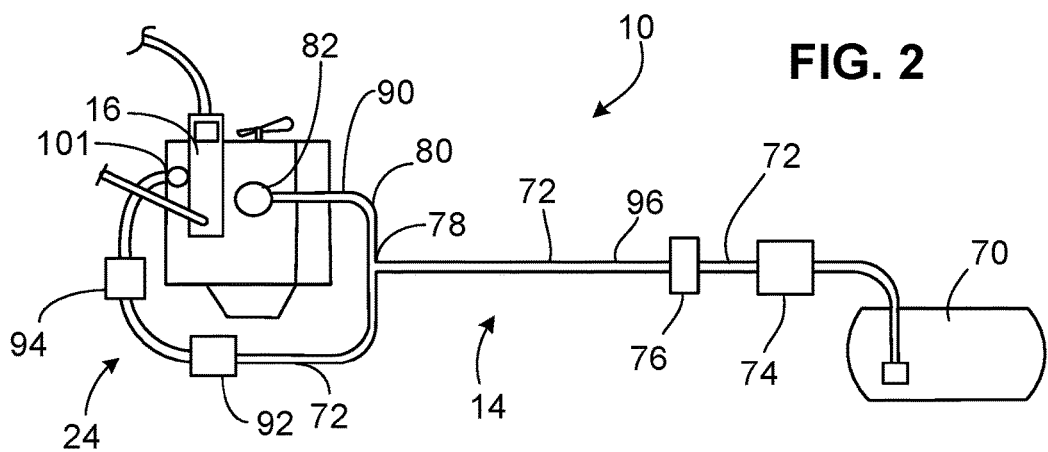
FIG. 2 is a schematic drawing of the fuel system.
Figure 3:
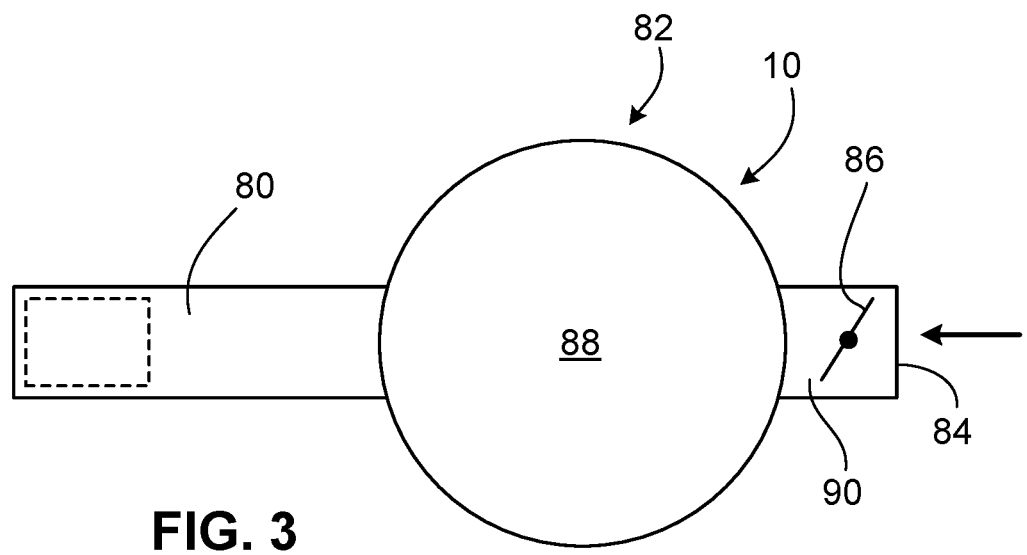
FIG. 3 is a top view of the throttle.
Figure 4:
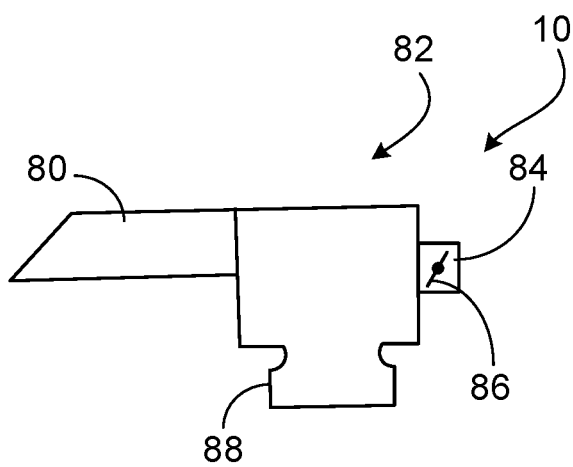
FIG. 4 is a side view of the throttle.

The Figures are selected to fully and completely demonstrate the preferred embodiment of the present invention and are not selected to show all conceivable modifications that would fall within the scope of the claim.

DETAILED DESCRIPTION

The present invention 10 thermally joins an exhaust system 12 and fuel system 14 in a vaporizer 16, forming a mist evaporator 18 and a boiler 20, the boiler 20 being integrated, e.g., using the same parts, with the mist vaporizer 18. The mist evaporator 18 and boiler 20 provide a synergistic effect most efficiently vaporizing fuel 22 to obtain an improved level of vaporization of the fuel 22 prior to entry into an internal combustion engine 24, hereinafter engine. The exhaust system 12 and fuel system 14 will be separately described, culminating in a description of the mist evaporator 18 and boiler 20.

Exhaust System

FIG. 1 is a schematic drawing of an overview of the exhaust system 12.

The engine 24, which produces exhaust 30, is joined to one or more exhaust outlets 32, which in turn is/are joined to the exhaust line 34. The exhaust line 34 extends from the engine 24 to the exhaust exit 38. Mid-length, the exhaust line 34 preferably joins to an exhaust valve 36. The exhaust valve 36 directs a portion of the exhaust 30 through a exhaust passageway 40 and directs the balance of the exhaust 30 through a recycling passageway 48, which will be described further below.

The sealed exhaust passageway 40, leading from the engine 24 to the exhaust exit 38 and to the atmosphere, is defined by exhaust outlets 32, exhaust line 34, exhaust valve 36, catalytic converter 42, muffler 44 and exit 38. The exhaust outlets 32 of the engine 24 are joined to the exhaust line 34 at an upstream end 46. The exhaust line 34 may be in various segments and be joined to the exhaust valve 36, catalytic converter 42, muffler 44 and exit 38. Exhaust 30 from the engine 24 is in flowable communication, through the exhaust passageway 40, with the atmosphere. Preferably, all the exhaust 30 from the engine 24 is ultimately in flowable communication, through the exhaust valve 36, with a catalytic converter 42, muffler 44 and the exhaust exit 38, although some exhaust 30 may flow through the exhaust valve 36 and recycling passageway 48 prior to the catalytic converter 42, muffler 44 and exhaust exit 38.

The recycling passageway 48 is joined to the exhaust passageway 40 such that exhaust 30 in the engine 24 is in flowable communication through the conduit 50 prior to the exhaust exit 38. Recycling passageway 48 may be defined by the exhaust valve 36, first recycling line 52, exhaust inlet 54, exhaust inlet chamber 56, conduit 50, exhaust outlet chamber 58, exhaust outlet 60 and second exhaust recycling line 62. The recycling passageway 48 extends from the exhaust valve 36, through the conduit 50, which may be in the vaporizer 16, and back to the exhaust line 34. Exhaust 30 in the exhaust passageway 40 is, therefore, in flowable communication through the entire recycling passageway 48 and back to the exhaust passageway 40.

The recycling passageway 48 will now be described with specific reference to the components defining the recycling passageway 48. A first exhaust recycling line 52 joins to the exhaust valve 36 and to the exhaust inlet 54 of the vaporizer 16, such that exhaust 30 from the engine 24 is in flowable communication with the vaporizer 16. A second exhaust recycling line 62 may join the exhaust outlet 60 of the vaporizer 16 to the exhaust line 34 either downstream or upstream of the exhaust valve 36, thereby providing a return. The second exhaust recycling line 62 joins to the exhaust outlet 60 and to the exhaust line 34 such that exhaust 30 in the vaporizer 16 (and first exhaust recycling line 52) is also in flowable communication with the exhaust line 34. The vaporizer 16, and more particularly the housing 64 and baffles 114 define the exhaust inlet chamber 56 and exhaust outlet chamber 58, which are in flowable communication through the conduit 50. The exhaust 30 in the vaporizer 16 is desirably not in flowable communication with the fuel 22.

Figure 5:
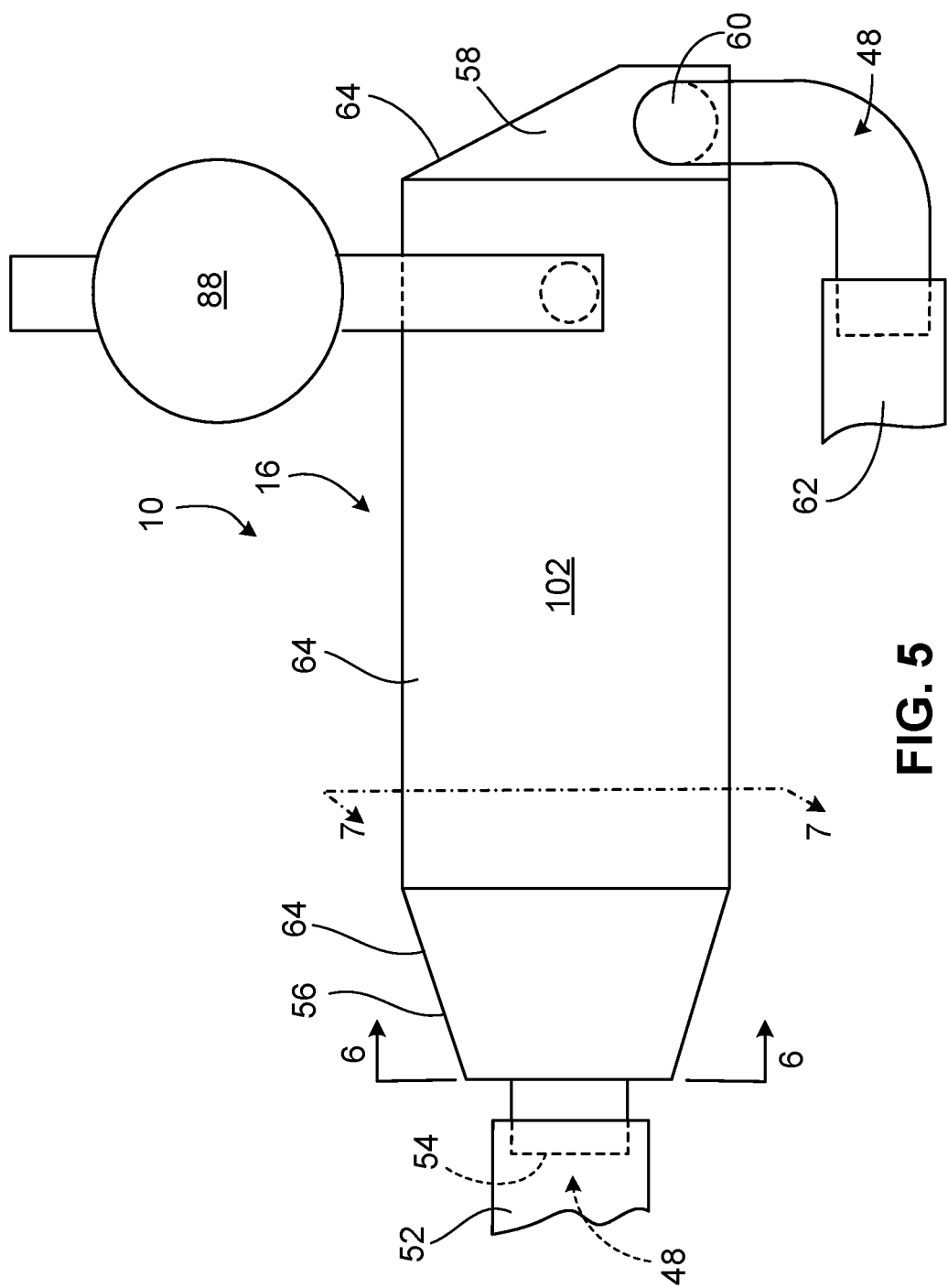
FIG. 5 is a side view of the vaporizer.
Figure 6:
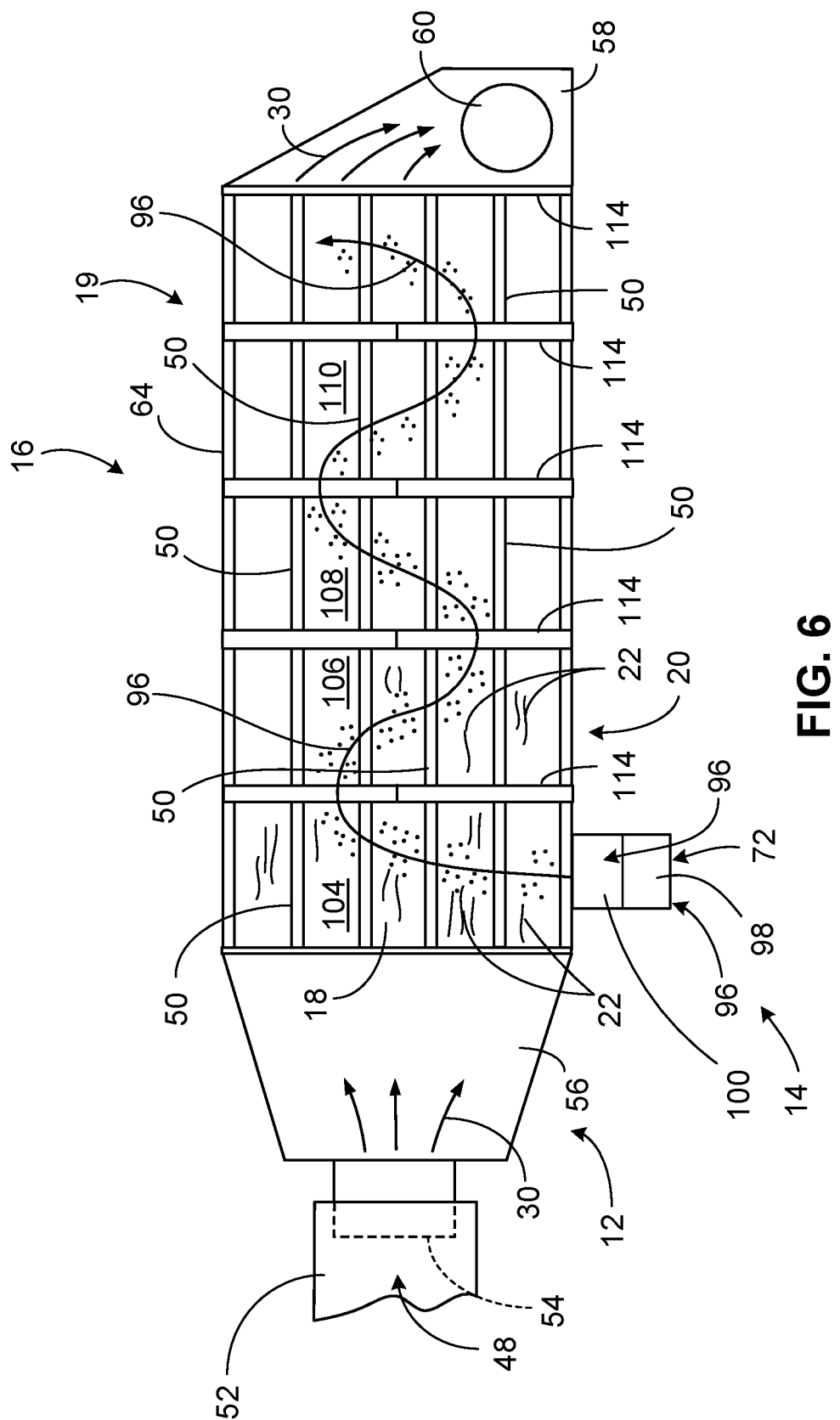
FIG. 6 is a sectional view taken along the lines 6-6 of FIG. 5.

The vaporizer 16, shown in greater specificity in FIGS. 5 and 6, forms a portion of the exhaust recycling passageway 48. FIG. 5 shows the exhaust inlet 54, housing 64 and exhaust outlet 60. The housing 64 may take any of a variety of shapes sizes and forms. Preferably, the housing 64 is formed of a high thermally conductive material such as copper, aluminum or other material known in the art. The housing 64 may define at least a portion of various chambers 56, 58, 104, 106, 108, 110, and 112, described here and throughout, within the vaporizer 16 (FIG. 6). The exhaust inlet chamber 54 may be approximately 3" by 5" by 5", the exhaust outlet chamber 58 may be 2" by 5" by 5", while the central chamber 102 may be 12" by 5" by 5". The exhaust inlet chamber 56 is sealably joined to and disposed between the exhaust inlet 54 and conduit 50. The exhaust outlet chamber 58 is sealably joined to and disposed between the conduit 50 and exhaust outlet 60. The conduit 50 is preferably formed of a high thermally conductive material such as aluminum, copper or other material known in the art.

Figure 7:
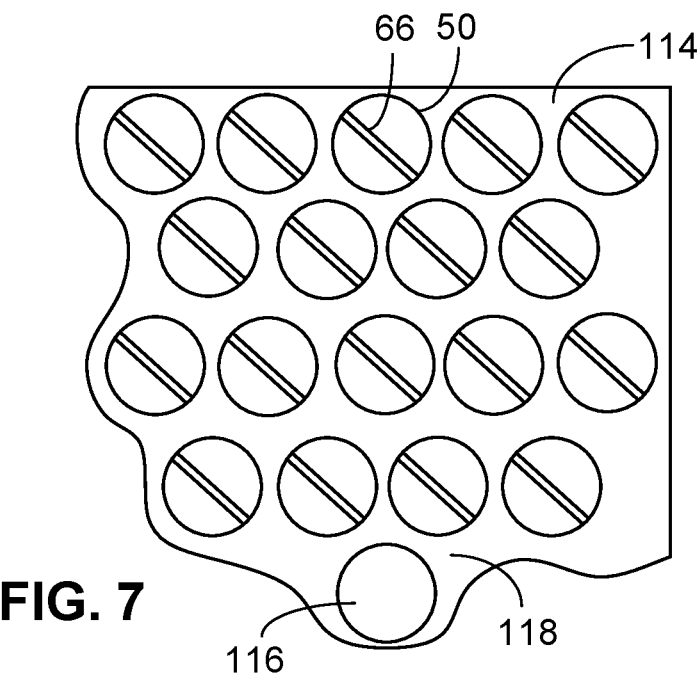
FIG. 7 is an end view of the central portion of the vaporizer taken along the lines 7-7 of FIG. 5, showing the conduit and turbulators.
Figure 8:
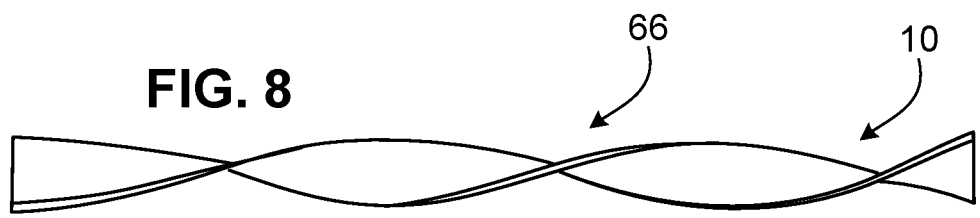
FIG. 8 is a side view of a turbulator.

The conduit 50 may be joined to a turbulator 66; preferably joined inside the conduit 50. A turbulator 66 is any mechanism suitable for causing turbulence in the conduit 50 such that the exhaust 30 thermally mixes within the conduit 50. A suitable turbulator 66 desirably is a piece of flat metal twisted into a spiral, see FIG. 8, having a width equivalent to an inside diameter of the conduit 50 as shown in FIG. 7. The turbulator 66 may have a length equivalent to the length of the conduit 50 and may be friction fit therein. One skilled in the art can see that alternative forms of turbulators 64 may be designed. In a preferred embodiment, the turbulator 66 is made from ⅛" aluminum stock, being ¾" wide by 12" long, twisted and put into ¾" aluminum conduit 50. The turbulators 66 distribute heat and slow down the flow of the exhaust 30.

The recycling lines 52, 62 and vaporizer 16 recycle heat energy from the exhaust 30 for use in vaporizing the fuel 22. The conduit 50, which defines a portion of the recycling passageway 48 as described above, is in thermal communication with the exhaust 30 and in thermal communication with the fuel 22 whether in a mist or liquid form. The exhaust 30 and fuel 22 are preferably only indirectly in thermal communication with each other via the conduit 50. That is, the exhaust 30 is contained within the conduit 50, while the fuel 22 is positioned outside the conduit 50.

In summary, the engine 24 is flowably joined to the exhaust system 12. The exhaust system 12, includes the exhaust passageway 40 that joins to the recycling passageway 48 at the exhaust valve 36. The exhaust valve 36 directs a portion of the exhaust 30 through to continuing portions of the exhaust passageway 40 and directs the balance of the exhaust 30 through the recycling passageway 48. The recycling passageway 48 provides mechanism for recycling heat energy from the exhaust 30 to the fuel 22. Exhaust 30 in the recycling passageway 48 is in flowable communication (in and out) with the exhaust passageway 40 and ultimately exits to the atmosphere.

Fuel System

The fuel system 10 includes a vaporizer 16 that conditions fuel 22 for combustion in the engine 24. The fuel system 10 may include a fuel tank 70 for fuel storage joined to a fuel line 72. The fuel line 72 may pass through various components in-line to the internal combustion engine 24. For instance, the fuel line 72 may join to a fuel filter 74, a fuel pump 76 and a T-splitter 78.

The T-splitter 78 allows fuel 22 to enter the engine 24, cylinders thereof, in a traditional manner. A fuel transfer tube 80 may join the T-splitter 78 to a throttle 82. The throttle 82 may have an inlet 84 joined to a throttle body 88. A choke 86 may be disposed adjacent the inlet 84 the throttle body 88. An air passageway 90, extending from the atmosphere to the throttle body 88, is therefore cooperatively defined by the inlet 84, choke 86, throttle body 88, allowing air to mix with the fuel 22 in the throttle body 88. Vapor (air) from the atmosphere is in flowable communication with fuel 22 through the air passageway 90. A switch disposed inside the passenger area of the vehicle may be used to switch the flow of fuel 22 at the T-splitter 78 to the throttle body 88 or alternatively to the vaporizer 16, depending upon the needs of power. It has been found that the need for increased power, e.g. vehicle is accelerating or climbing hills, is more efficiently met when the fuel 22 flows through the throttle 82 and cruising is more efficient through the vaporizer 16.

The fuel line 72, downstream of the T-splitter 78, may flowably join to a second fuel filter 92, a flow meter 94 and the vaporizer 16. The vaporizer 16 may be joined to the internal combustion engine 24. The fuel tank 70, fuel line 72, fuel filter 74, fuel pump 76, T-splitter 78, second fuel filter 88, flow meter 94, vaporizer 16 and engine 24 thus define a fuel passageway 96. Fuel 22 from the tank 70 is in flowable communication through the fuel passageway 96 with the engine 24. The fuel 22 is combusted in the engine 24, generating exhaust 30.

The fuel line 72 may be joined to an injector 98 and flowably joined to an atomizer 100, which in turn are joined to the vaporizer 16. An atomizer 100 is fine mesh screen sized and adapted to split fuel 22 into a mist when the injector 98 propels fuel 22 against the atomizer 100. Desirably, the injector 98 and atomizer 100 are positioned adjacent a first chamber 104 of the central portion 102 of the vaporizer 16 such that the fuel 22, in mist form, may enter into a first chamber 104 of the central portion 102 of the vaporizer 16 above any fuel 22 that may be pooled therein. Most desirably, the injector 98 and atomizer 100 are joined to a throttle body 101, similar to that described above and otherwise known in the art. The throttle body 101 may allow butterfly valves to open upon depression of the gas peddle to allow air to mix with the misted fuel. The butterfly valves and connection to the gas peddle is technology known in the art.

Figure 9:
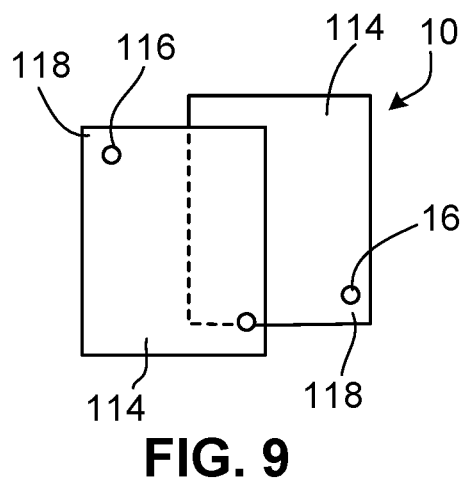
FIG. 9 is a perspective view of adjacent baffles with the conduit removed.
Figure 10:
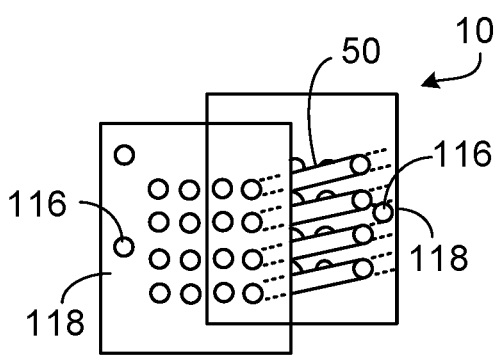
FIG. 10 is a perspective view of adjacent baffles with the conduit shown in partial phantom.

The vaporizer 16 desirably includes baffles 114 which join to the housing 64 to define a plurality of chambers, such as chambers 104, 106, 108, 110 and 112, each chamber being sized and adapted to hold a pool of fuel 22. The chambers 104, 106, 108, 110 and 112 are intended to be positioned approximately side-by-side. The baffles 114 are desirably of a highly thermally conductive material such as aluminum, copper or other material known in the art. The baffles 114 may sealably join to the housing 64 about the perimeter of each baffle 114. Similarly, the baffles 114 may sealably join to the conduit 50, preventing vapor flow therebetween. The conduit 50 extends through the baffles 114 and chambers 104, 106, 108, 110 and 112. FIG. 9 shows the baffles 114 defining apertures 116 in opposing portions 118 of adjacent baffles 114 with the conduit 50 removed for clarity. "Opposing portions" 118 is a relational term between adjacent baffles 114 that is defined such that vapor flowing through the apertures 116 of a first baffle 114 will generally flow through a matrix of conduit 50 to pass through the aperture 116 in the next baffle 114. The matrix of conduit 50 may include eighteen, more or less, ¾" by 12" aluminum tubes. Opposing portions 118 may be diagonal as shown in FIG. 9, right and left sides (See FIG. 10), top and bottom or oriented in generally opposite directions of the center. FIG. 10 is similar to FIG. 9, but with the conduit 50 in place such that the tortuous path of vapors is readily apparent.

Fuel 22 in the first chamber 104 is in flowable communication with the chambers 100, 102, 104 and 106 through apertures 116. Fifth chamber 112, assuming five chambers are present, is joined to an outlet 120, which in turn is joined to engine 24. Fuel 22 in the fifth chamber 112 is in flowable communication with the engine 24.

Mist Evaporator and Boiler

From the above description, one skilled in the art will notice that the fuel mist 22 flows through a highly tortuous path. Conversely, fuel 22 that is not well vaporized, e.g. large droplets, will not fully travel the length of the tortuous path and will pool in one of the chambers 104, 106, 108, 110, or 112. The baffles 114 with apertures 116 in combination with the housing 64, which define chambers 104, 106, 108, 110, and 112, and conduit 50, therefore, constitute a mist evaporator 18 converting the fuel 22 in mist form to vapor fuel 22. The baffles 114 and housing 64 define a portion of the fuel passageway 96 through which fuel 22 in mist form may pass, while the conduit 50 vaporizes the mist.

The fuel droplets 22 that are too large for traveling the tortuous path temporarily form a pool in one of the chambers 104, 106, 108, 110, and 112. The conduit 50, baffles 114 and housing 64 are all of highly thermally conductive material and cooperatively form a boiler 20. The conduit 50 is in thermal communication with the baffles 114. The baffles 114 are in thermal communication with the housing 64. The baffles 114 and housing 64 contain and are in thermal communication with a pool of fuel 22. Heat energy from the conduit 50 is thermally conducted to the baffles 114 and housing 64, which in turn transfer the heat energy to the fuel 22 causing evaporation. The housing 64, baffles 114, and conduit 50 may simultaneously be a mist vaporizer 18 and boiler 20. That is, the mist vaporizer 18 and boiler 20 are integrated.

The conduit 50 aids in converting fuel 22 in mist form into vapor capable of traveling the tortuous path and also adds to the tortuous nature of the fuel passageway 96 inside the vaporizer 16. The conduit 50, which may be in thermal communication with the exhaust 30 and may be in thermal communication with the fuel 22 in a mist form, transfers heat energy from the exhaust 30 contained in the conduit 50 to the fuel 22. Fuel 22 in a mist form may be refined into vapor suitable for traveling the fuel passageway 96. The conduit 50 transfers heat energy from the exhaust 30 to the baffles 114 and housing 64, which in turn transfer the heat energy to the fuel 22, pooled in any of the chamber 104, 106, 108, 110, and 112, causing evaporation and making the fuel 22 sufficiently vaporized to travel the fuel passageway 96. The conduit 50 is preferably arranged in a matrix suitable for enhancing the tortuous nature of the fuel passageway 96.

The number of chambers is one factor that has been found important to the completeness of the vaporization process. When too few chambers are used, pooling of fuel 22 can occur faster than the boiling and the mist does not fully vaporize. Increasing the number of chambers increases the vaporization of the fuel 22 whether in pool or mist form. The preferred number of chambers is five, as shown, given the dimensions of the other components. One skilled in the art can see that altering the other components will impact the preferred number of chambers. Each of the chambers 104, 106, 108, 110, and 112 preferably define an internal area that is larger than the area contained within the conduit 50, since the fuel 22, not the exhaust 30, expands in volume inside the vaporizer 16.

In Operation

The engine 24 combusts fuel 22, creating exhaust 30. The exhaust 30 flows out through the exhaust outlet 32 into the exhaust line 34. Exhaust 30 divides into two portions at the exhaust valve 36, sending one portion through the recycling passageway 48 and the balance remains in the exhaust passageway 40. Exhaust 30 in the recycling passageway 48 is moved into the vaporizer 16 and more particularly inside the conduit 50 inside the vaporizer 16. Heat energy from the exhaust 30 is transferred to the fuel 22 directly and indirectly through the conduit 50 to vaporize the fuel 22. Thereafter, the exhaust 30 is directed back into the exhaust passageway 40. Exhaust 30 in the exhaust passageway 40 downstream of the exhaust valve 36 may pass through various conditioning apparatus such as a catalytic converter 42 and muffler 44 prior to being released into the atmosphere.

Simultaneously, fuel pump 76 draws and pushes the fuel 22 from the fuel tank 70 into the fuel line 72 and ultimately into the vaporizer 16 and engine 24. The fuel 22 may be conditioned in the fuel filter 74, t-splitter 78, either throttle 88 or alternatively injector 98, atomizer 100, and vaporizer 16. Fuel 22, passing through the throttle 88 and into the engine 24 does so in a standard manner. The flow of the fuel 22 may be switched away from the throttle 88 and to the vaporizer 16.

When fuel 22 is directed to the vaporizer, the flow meter 94 controls the flow rate of the fuel 22 to the vaporizer 16. The injector 98 propels fuel 22 at the atomizer 100, splitting the fuel 22 into a mist form. The mist enters the first chamber 104, receiving heat energy indirectly from the exhaust 30. Inside the vaporizer 16, the liquid fuel 22 from the mist may pool. Fuel 22 in a mist form travels through the matrix of conduit 50 and apertures 116 while being converted to vapor. Fuel 22 in pools is maintained inside one or more of the chambers 104, 106, 108, 110, and 112. The liquid fuel 22 is boiled until it achieves vaporization and can then travel the fuel passageway 96 into the engine 24. The engine 24, thereafter, combusts the vaporized fuel 22.

The present invention has been described with reference to the drawings in a manner to fully disclose the best mode of making and using the present invention. The description is explanatory in nature and is not intended to identify and describe all possible modifications that fall within the scope of the claims. Substantive and material changes may be made without departing from the spirit and scope of the present invention.

Direct Fuel Injection

Figure 11:
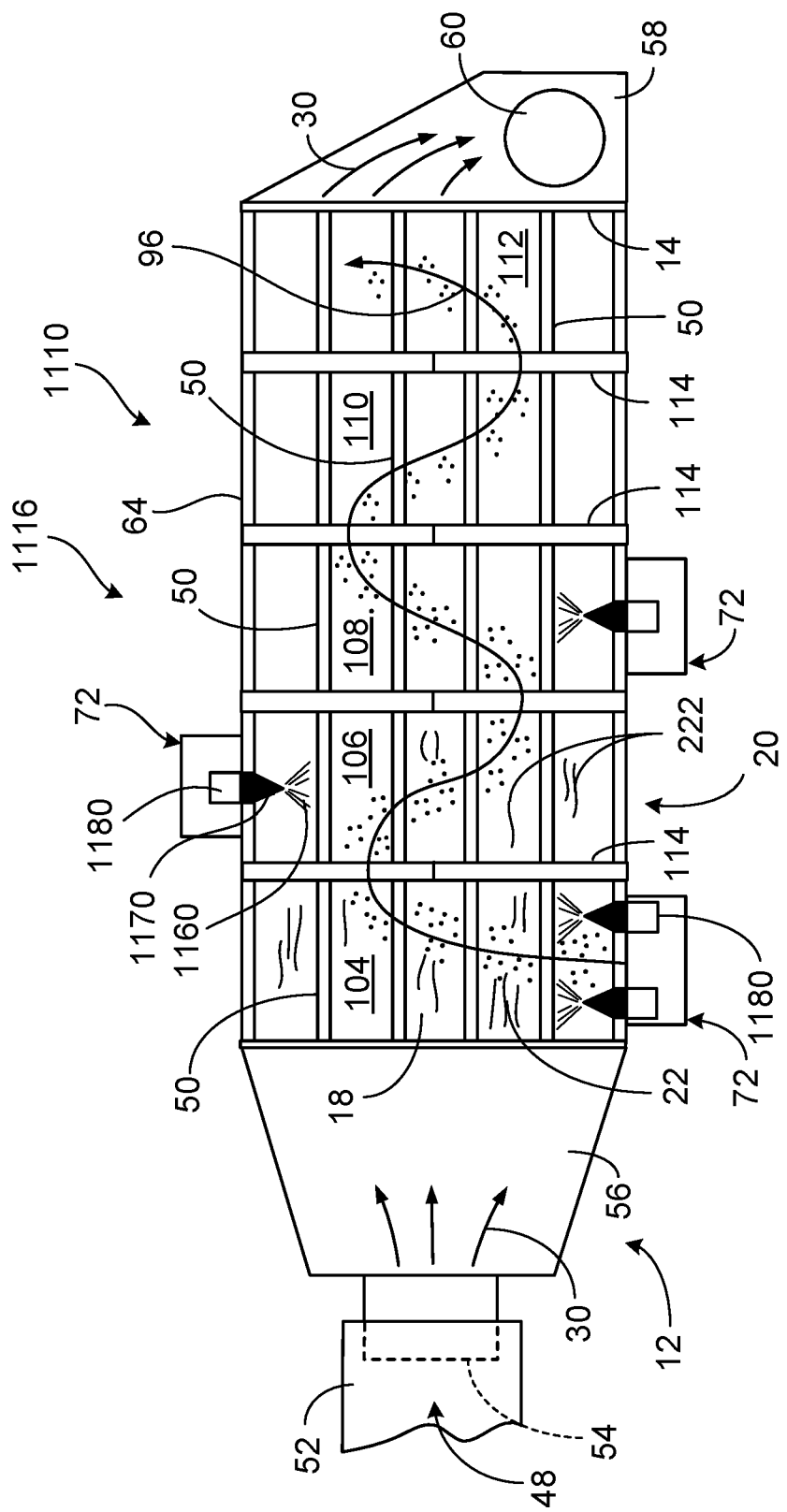
FIG. 11 is a schematic of a fuel vaporizer with fuel injectors.

FIG. 11 is a schematic of a fuel vaporizer with fuel injectors. and a heat exchanger. FIG. 11 shows a fuel system 1100 including a vaporizer 1116 having a plurality of chambers 104, 106, 108, 110, 112 and a plurality of fuel injectors 1180 instead of a carburetor system. Each fuel injectors 1180 having nozzles 1170 extending into the housing 64 of the vaporizer 1116 to direct inject fuel 22 into the chambers 104, 106, 108, 110, 112. The nozzles 170 create a spray 1160 of fuel 22 in, for example, the first chamber 104. The spray 1160 of fuel 22 may be an atomized mist of fuel 22. The fuel pump 76 draws and pushes the fuel 22 from the fuel tank 70 into the fuel line 72 and ultimately into the nozzles 1170 of the fuel injectors 1180.

In operation, an airflow supplied to the first chamber 104 of the vaporizer 1116 encounters the spray 1160 of fuel 22 from the nozzle 1170 of the fuel injector 1180. The airflow travels the fuel passageway 96 through the first chamber 104, and the conduits 50 heat the airflow and fuel 22 to vaporize a portion of the fuel 22 into the airflow. The airflow and fuel 22 travel the fuel passageway 96 into the remaining chambers 106, 108, 110, 1112 and conduit to be heated by the conduits 50, resulting in increased vaporization of the fuel 22 into the airflow.

In addition to the number of chamber, the number and location of the fuel injectors 1180 is another factor that has been found important to the completeness of the vaporization process. Increasing the number of injectors in each chamber, or the number of chambers having injectors affects the vaporization of the fuel 22. In some aspects, the first chamber 104 includes two fuel injectors 1180 and the second 106 and third chambers 108 include one fuel injector each. One skilled in the art can see that altering the other components will influence the preferred number of injectors. In some aspects, the vaporizer is designed to create 80% saturation of the fuel 22 in the airflow through fuel passageway 96 at the exit from the fuel vaporizer 1116.

Another factor that is important in the operation of the fuel injection vaporizer 1116 is the temperature of the airflow though the plurality of chambers 104, 106, 108, 110, 112. One skilled in the art can see that altering the components will influence the temperature of the airflow through each chambers. In some examples, the airflow though the fuel passageway 96 exits the first chamber 104 at 750° F. In some examples, the airflow though the fuel passageway 96 exits the fifth chamber 112, or the final chamber, at 450° F. In some examples, the airflow though the fuel passageway 96 is delivered to the internal combustion engine 24 at 375° F. One skilled in the art can see that altering the properties or types of fuel 22 will influence the temperatures necessary to achieve a desired vaporization of the fuel 22 though the fuel passageway 96.

Heat Exchanger

FIGS. 12A and 12B are schematics of a fuel vaporizer with fuel injectors. FIG. 12A shows a heat exchanger 1201 including a plurality of baffles 1212 forming an air pathway 95 from an air intake 1202 to an aperture 1203 into the first chamber 104 of the housing 64 of the fuel vaporizer 1116. In operation, the heat exchanger 1201 is positioned adjacent to the housing 64 of the fuel vaporizer 1116 and transfers thermal energy from the housing 64 of the fuel vaporizer 1116 to an airflow in the air pathway 31. In some examples, the heat exchanger 1201 improves the operation of the fuel vaporizer 1116 by increasing the temperature of the airflow entreating the first chamber 104, which results in faster heating of the airflow in the first chamber 104 and increased vaporization of fuel 22 in the airflow in the first chamber 104.

FIG. 12B shows a vaporizer system 1210 including a heat exchanger 1201 and a fuel vaporizer 1116. FIG. 12B is a cross section of a fuel vaporizer 1116 through the first chamber 104. The conduits 50 passing through the baffle 114 of the first chamber 104 are visible, as are turbulators positioned in the conduits 50. The heat exchanger 1201 includes an air intake 1202 accepting a flow of air and an aperture 1203 into the first chamber 104 of the housing 64 of the fuel vaporizer 1116. The heat exchanger 1201 is thermally coupled with the housing 64 of the fuel vaporizer 1116. FIG. 12B shows a nozzle 1170 of a fuel injector 1160 positioned adjacent to the air pathway 95 from the heat exchanger 1201 entering the first chamber 104. An atomized spray 1180 of fuel is shown in the air pathway 95, where the fuel passageway 96 begins. The fuel passageway 96 passes through the conduits 50 and into an aperture 115 leading to the second chamber 106.

FIG. 12B also shows electric heating elements 1290, 1291 thermally coupled with the fuel vaporizer 1116. A first set of electric heating elements 1290 runs along the conduits 50, and a second set of electric heating elements 1291 are coupled to the baffle 114 between the first chamber 104 and the second chamber 106. The electric heating elements 1290, 1291 are in the fuel passageway 96 and enable electric power to heat the conduits 50 and the baffle 114 and, therefore, transfer thermal energy to the airflow in the fuel passageway 96.

In operation, the electric heating elements 1290, 1291, in some instances, supplement to the heat transfer from the exhaust gas 30 in the conduits, in order to maintain desired airflow temperatures or vaporization levels along fuel passageway 96. For example, if the internal combustion engine 24 is at an idle condition, the thermal output from the exhaust gas 30 may not be sufficient to maintain a desired vaporization level of fuel 22 in the fuel passageway 96, and the electric heating elements 1290, 1291 are used to maintain the desired vaporization level of fuel 22 entreating the internal combustion engine 24 to maintain operation. In some instances, the electric heating elements 1290, 1291 are powered by a battery onboard a vehicle having the internal combustion engine 24. The vehicle may be an electric hybrid vehicle having a primary electric motor providing propulsion, and an internal combustion engine 24 operating a generator to supply the electric motor with power directly, or to a battery system supplying the electric motor. In some instances, the internal combustion engine 24 is mechanically coupled to a generator for steady-rpm changing of the battery. The electric heating elements 1290, 1291 may be used, for example, to maintain regulate the airflow temperatures or vaporization levels along fuel passageway 96 if, for example, the power demand of the internal combustion engine 24 drops.

In some instances, the electric heating elements 1290, 1291 enable a cold-start of the internal combustion engine 24 by pre-heating the conduits 50 and baffles 114 before the internal combustion engine 24 is started, and the while internal combustion engine 24 is warming up. In some instances, the internal combustion engine 24 includes a traditional fuel injection system that operators the internal combustion engine 24 during a cold-start, and the fuel injector system 1210 is heated by the exhaust gas 30 until the vaporized 1116 is able to supply vaporized fuel 22 to the internal combustion engine 24. Once vaporized fuel 22 is delivered to the internal combustion engine 24, the traditional fuel injection system may be disabled.

There has been described novel apparatus and techniques in connection with fuel vaporization using fuel injectors. It is evident that those skilled in the art may make numerous modifications of and departures from the specific apparatus and techniques herein disclosed without departing from the inventive concepts. Consequently, the invention is to be construed as embracing each and every novel concept and combination of concepts disclosed herein and limited only by the spirit and scope of the appended claims.

What is claimed is:

1. A fuel vaporizer, comprising: a housing comprising: a plurality of baffles joined to the housing, the housing and baffles defining a plurality of chambers, each of the plurality of baffles defining an aperture between adjacent chambers, an air inlet in a first chamber of the plurality of chambers, an vapor outlet in a last chamber of the plurality of chambers, the apertures defining a flow path from the air inlet, through the plurality of chambers, and to the vapor outlet, and a conduit extending through the baffles and chambers, the conduit adapted to accept a flow of exhaust gas there through, the conduit positioned in the flow path, and the conduit adapted to transfer thermal energy from the exhaust gas to an airflow along the flow path; and a fuel injector positioned in an opening in the housing, the fuel injector adapted to inject fuel into the flow path in the first chamber, wherein the housing is adapted to accept the airflow at the air inlet and produce a flow of vaporized fuel to the vapor outlet, the thermal energy from the conduit vaporizing the fuel injected into the airflow and producing the flow of vaporized fuel.

2. The fuel vaporizer of claim 1 wherein the fuel vaporizer defines an exhaust inlet chamber and an exhaust outlet chamber in flowable fluid communication through the conduit.

3. The device of claim 1, wherein the conduit is a matrix of a plurality conduits.

4. The device of claim 1, wherein the conduit includes a turbulator joined inside the conduit.

5. The fuel vaporizer of claim 1, further including an electric heating element adapted to heat the conduit, the heating element enabling electric heating of the airflow through the flow path.

6. The fuel vaporizer of claim 5, wherein the heating element is integrated with the plurality of baffles.

7. The fuel vaporizer of claim 5, wherein the heating element is integrated with the conduit.

8. The fuel vaporizer of claim 1, further including: a heat exchanger in thermal connection with the outer surface of the housing, the heat exchanger defining an internal flow path in flowable fluid communication with the air inlet of the housing, the heat exchanger being adapted to heat the airflow along the internal flow path with thermal energy from the housing prior to the airflow entering the air inlet of the housing.

9. The fuel vaporizer of claim 1, wherein the fuel injector is a first fuel injector in a first opening in the housing, the fuel vaporizer further comprising a second fuel injector positioned in a second opening in the housing, the second fuel injector adapted to inject fuel into the flow path in the first chamber.

10. The fuel vaporizer of claim 1, wherein the fuel injector is a first fuel injector in a first opening in the housing, the fuel vaporizer further comprising a second fuel injector positioned in a second opening in the housing, the second fuel injector adapted to inject fuel into the flow path in a second chamber, the second chamber being adjacent to the first chamber.

11. The fuel vaporizer of claim 10, further comprising a third fuel injector positioned in a third opening in the housing, the third fuel injector adapted to inject fuel into the flow path in a third chamber, the third chamber being adjacent to the second chamber.

12. A method of operating an internal combustion engine, given a fuel, an airflow, and exhaust gas from the internal combustion engine, the method comprising:
flowing the exhaust gas through a conduit, the conduit passing through a plurality of chambers formed by a plurality of baffles, the exhaust gas transferring thermal energy to the conduit;
flowing the airflow through the plurality of chambers, the airflow flowing around the conduit;
injecting the fuel in the airflow of a first chamber of the plurality of chambers, the injecting atomizing the fuel in the airflow;
transferring thermal energy from the conduit to the airflow in the plurality of chambers, the thermal energy vaporizing at least a portion of the fuel in the airflow and generating a flow of vaporized fuel; and
providing the flow of vaporized fuel to an intake of the internal combustion engine.

13. The method of claim 12, wherein flowing the exhaust gas through a conduit comprises flowing the exhaust gas through a matrix of a plurality of conduits.

14. The method of claim 13, wherein flowing the airflow through the plurality of chambers comprises flowing the airflow through the matrix of the plurality of conduits in each of the plurality of chambers.

15. The method of claim 12, wherein flowing the exhaust gas through a conduit further comprises adding turbulence to the flow of exhaust gas inside the conduit.

16. The method of claim 12, further including injecting the fuel in the airflow in a second chamber of the plurality of chambers.

17. The method of claim 12, wherein transferring thermal energy from the conduit to the airflow in the plurality of chambers comprises heating the airflow in the first chamber to at least 725 degrees Fahrenheit.

18. The method of claim 17, wherein transferring thermal energy from the conduit to the airflow in the plurality of chambers comprises heating the airflow in a last chamber to at least 450 degrees Fahrenheit.

19. The method of claim 12, wherein the thermal energy vaporizing at least a portion of the fuel in the airflow, comprises vaporizing at least 50% of the fuel.

20. The method of claim 12, wherein the thermal energy vaporizing at least a portion of the fuel in the airflow, comprises vaporizing at least 80% of the fuel.

21. The method of claim 12, further comprising transferring thermal energy to the conduit with an electric heating element.

22. The method of claim 21, wherein transferring thermal energy to the conduit with an electric heating element comprises regulating a temperature of the airflow using the transferring of thermal energy to the conduit from the electric heating element.

23. The method of claim 22, wherein the regulating based on a temperature of one or more of the following: the exhaust gas, the conduit, and the airflow.

24. The method of claim 12, wherein flowing the exhaust gas through a conduit comprises regulating the flow of exhaust gas through the conduit to maintain a temperature of the airflow in at least one of the first chamber and the intake.

25. The method of claim 12, further including:
prior to the injecting the fuel in the airflow of a first chamber, starting the internal combustion engine using a fuel injection system of the internal combustion engine, and
transitioning from the fuel injection system of the internal combustion engine to injecting the fuel in the airflow of a first chamber, the transitioning being based on a temperature of the airflow or a temperature of the conduit.

26. A method of operating an internal combustion engine, given a fuel, an airflow, and exhaust gas from the internal combustion engine, the method comprising:
flowing the exhaust gas through a conduit, the conduit passing through a plurality of chambers formed by a plurality of baffles,
flowing the airflow through the plurality of chambers, the airflow flowing around the conduit;
injecting the fuel in the airflow of a first chamber of the plurality of chambers, the injecting atomizing the fuel in the airflow;
transferring thermal energy from an electric heating element to the airflow in the plurality of chambers, the thermal energy vaporizing at least a portion of the fuel in the airflow and generating a flow of vaporized fuel; and
providing the flow of vaporized fuel to an intake of the internal combustion engine.

* * * * *

UNITED STATES PATENT AND TRADEMARK OFFICE
CERTIFICATE OF CORRECTION

PATENT NO. : 10,094,342 B2
APPLICATION NO. : 15/456189
DATED : October 9, 2018
INVENTOR(S) : Dean Johanning Page 1 of 1

It is certified that error appears in the above-identified patent and that said Letters Patent is hereby corrected as shown below:

On the Title Page

Column 2, Abstract, Line 10, delete "path" and insert -- path. --, therefor.

In the Claims

Column 12, Claim 1, Lines 36-37, delete "there through," and insert -- therethrough, --, therefor.

Column 12, Claim 3, Line 51, delete "device" and insert -- fuel vaporizer --, therefor.

Column 12, Claim 4, Line 53, delete "device" and insert -- fuel vaporizer --, therefor.

Signed and Sealed this
Fifth Day of November, 2019

Andrei Iancu
*Director of the United States Patent and Trademark Office*